United States Patent [19]
Liu et al.

[11] Patent Number: 5,279,783
[45] Date of Patent: Jan. 18, 1994

[54] PROCESS FOR MANUFACTURE OF POLYAMIDE MONOFILAMENT SUTURE

[75] Inventors: Cheng-Kung Liu, Norwalk; John C. Brewer, Bristol, both of Conn.

[73] Assignee: United States Surgical Corporation, Norwalk, Conn.

[21] Appl. No.: 828,010

[22] Filed: Jan. 30, 1992

[51] Int. Cl.$^5$ .............. D01F 6/60; D01F 8/12
[52] U.S. Cl. .............. 264/178 F; 264/210.8; 264/211.15; 264/235.6; 264/289.6; 264/290.5; 264/331.19; 606/228
[58] Field of Search .......... 264/210.8, 342 RE, 210.7, 264/211.14, 235.6, 176.1, 289.6, 290.5, 290.7, 211.15, 178 R, 178 F, 331.19; 606/231, 224, 225, 227, 228

[56] References Cited

U.S. PATENT DOCUMENTS

| | | |
|---|---|---|
| 2,212,772 | 8/1940 | Graves . |
| 2,226,529 | 12/1940 | Austin . |
| 3,091,015 | 5/1963 | Zimmerman . |
| 3,124,632 | 3/1964 | Larkin et al. ............ 264/289.6 |
| 3,156,750 | 11/1964 | Cululo ............ 264/342 RE |
| 3,303,169 | 2/1967 | Pitzl . |
| 3,311,691 | 3/1967 | Good ............ 264/235.6 |
| 3,345,445 | 10/1967 | Siclari et al. . |
| 3,361,859 | 1/1968 | Cenzato . |
| 3,379,810 | 4/1968 | Ciceri et al. . |
| 3,436,450 | 4/1969 | Specker et al. ............ 264/342 RE |
| 3,562,382 | 2/1971 | Fowler ............ 264/342 RE |
| 3,577,500 | 4/1971 | Kohler et al. . |
| 3,739,055 | 6/1973 | Ueda et al. ............ 264/342 RE |
| 3,792,010 | 2/1974 | Wasserman et al. ............ 606/231 |
| 4,009,511 | 3/1977 | Gauntt . |
| 4,338,277 | 7/1982 | Saito et al. ............ 264/235.6 |
| 4,374,797 | 2/1983 | Koschinek et al. . |
| 4,446,299 | 5/1984 | Koschinek et al. . |
| 4,461,740 | 7/1984 | Koschinek et al. . |
| 4,470,941 | 9/1984 | Kurtz ............ 264/134 |
| 4,504,432 | 3/1985 | Kamei et al. . |
| 4,504,545 | 3/1985 | Kurita et al. . |
| 4,542,063 | 9/1985 | Tanji et al. . |
| 4,550,730 | 11/1985 | Shalaby et al. ............ 606/231 |
| 4,578,451 | 3/1986 | Weaver et al. . |
| 4,621,021 | 11/1986 | Kitamura et al. . |
| 4,624,816 | 11/1986 | Kurita et al. . |
| 4,701,377 | 10/1987 | Kurita et al. . |
| 4,758,472 | 7/1988 | Kitamura et al. . |
| 4,839,132 | 7/1989 | Wang . |
| 4,859,389 | 8/1989 | Kurita et al. . |
| 5,007,922 | 4/1991 | Chen et al. ............ 606/228 |
| 5,102,420 | 4/1992 | Hunter et al. ............ 427/2 |
| 5,217,485 | 6/1993 | Liu et al. ............ 606/228 |

FOREIGN PATENT DOCUMENTS

| | | | |
|---|---|---|---|
| 0415783 | 3/1991 | European Pat. Off. ............ 606/231 |
| 53-24417 | 3/1978 | Japan ............ 264/210.8 |
| 54-27023 | 3/1979 | Japan ............ 264/210.8 |
| 57-139513 | 8/1982 | Japan ............ 264/342 RE |
| 59-157314 | 9/1984 | Japan ............ 264/289.6 |

*Primary Examiner*—Jeffery Thurlow

[57] ABSTRACT

A process for manufacturing polyamide monofilament suture includes the steps of extruding a polyamide resin, stretching the solidified monofilament and annealing the stretched monofilament so that it shrinks to within about 80 to about 97 percent of the length of the monofilament prior to annealing. The polyamide monofilament sutures so produced exhibit reduced energy compared to conventional polyamide monofilament sutures.

15 Claims, 1 Drawing Sheet

PROCESS FOR MANUFACTURE OF POLYAMIDE MONOFILAMENT SUTURE

BACKGROUND OF THE INVENTION

This invention relates to a polyamide (nylon) monofilament suture exhibiting improved properties, e.g., reduced energy and/or improved knot security, and to a process for its manufacture.

A considerable body of patent literature exists with regard to the manufacture of polyamide monofilaments. Illustrative of the many processes which have been developed over the years for the melt spinning of polyamide strands (filament, yarn, etc.) are those described in U.S. Pat. Nos. 2,212,772; 2,226,529; 3,091,015; 3,303,169; 3,345,445; 3,361,859; 3,379,810; 3,382,307; 3,577,500; 4,009,511; 4,374,797; 4,446,299; 4,461,740; 4,504,432; 4,504,545; 4,542,063; 4,578,421; 4,621,021; 4,624,816; 4,701,377; 4,758,472; 4,839,132; and, 4,859,389.

The manufacture of polyamide monofilaments which are intended for use as sutures is an established technology. U.S. Pat. No. 2,226,529 describes the melt spinning of polyhexamethylene adipamide (nylon 6,6) in which the resin is melt extruded and stretched to produce an oriented monofilament which is then heat treated to improve its recovery from deformation. A similar process resulting in a polyamide monofilament suture is described in U.S. Pat. No. 2,212,772. U.S. Pat. No. 4,578,451 describes a surgical filament manufactured from a copolyetheramide employing specific conditions for the extruding, quenching, drawing (stretching) and annealing operations.

One important characteristic of a suture is the amount of effort typically required to straighten the suture upon its removal from the package in order to ready the suture for use. In the case of a polyamide monofilament suture, this effort appears to be related to the "energy" of the suture, i.e., the integration of the stress-strain curve for the suture measured in kilograms, and is equivalent to the work expended in elongating the monofilament by a specified percentage of its original length. As the energy of a given size of polyamide monofilament suture is less so, too, the amount of effort required to straighten the suture prior to use is less.

Another important characteristic of a suture is its ability to retain a knot. In general, a suture exhibiting greater knot security is to be preferred to one exhibiting a lesser degree of knot security.

SUMMARY OF THE INVENTION

In accordance with the present invention, a process for manufacturing a polyamide monofilament suture exhibiting reduced energy and/or increased knot security for a given size is provided which comprises the operations of extruding a polyamide resin at an extrusion temperature of from about 215° to about 275° C. to provide a monofilament, stretching the solidified monofilament at a temperature of from about 40° to about 98° C. in water (or other suitable liquid medium) or at from about 50° to about 185° C. in air (or other suitable gaseous medium) at a stretch ratio of from about 3:1 to about 5:1 to provide a stretched monofilament and annealing (relaxing) the stretched monofilament at a temperature of from about 100° to about 180° C. to provide the finished suture, the annealing resulting in shrinkage of the stretched monofilament for a recovery to within about 80% to about 97% percent of the length of the monofilament prior to annealing, the finished suture exhibiting reduced energy and/or increased knot security compared with the energy and/or knot security of a suture of equivalent size and identical polymer obtained by a process which omits or deviates significantly from one or more of the foregoing operations.

The reduced energy of the polyamide monofilament suture of this invention represents a benefit which is enthusiastically appreciated by surgeons and their assistant personnel who will expend less time and effort in preparing the suture for use. Moreover, the greater knot security which is characteristic of the polyamide monofilament suture herein is highly desirable for the added measure of reliability and confidence it brings to the task of achieving successful wound closure.

DESCRIPTION OF THE PREFERRED EMBODIMENTS

A preferred polyamide monofilament manufacturing operation in accordance with the present invention includes the operations of extruding the polyamide resin, advantageously a polycaprolactam or a polyhexamethylene adipamide possessing a number average molecular weight of at least about 14,000 and a melt flow index in g/10 min of from about 3 to about 8, at an extrusion temperature of from about 220° to about 250° C., stretching the solidified monofilament at a temperature of from about 60° to about 98° C. in liquid medium, advantageously water, or from about 100° to about 170° C. in gaseous medium, advantageously air, at a stretch ratio of from about 3.5:1 to about 4.5:1 and annealing the stretched monofilament at a temperature of from about 120° to about 180° C. to effect shrinkage of the monofilament to within about 85% to about 97% of its length prior to annealing.

Figure 1A:
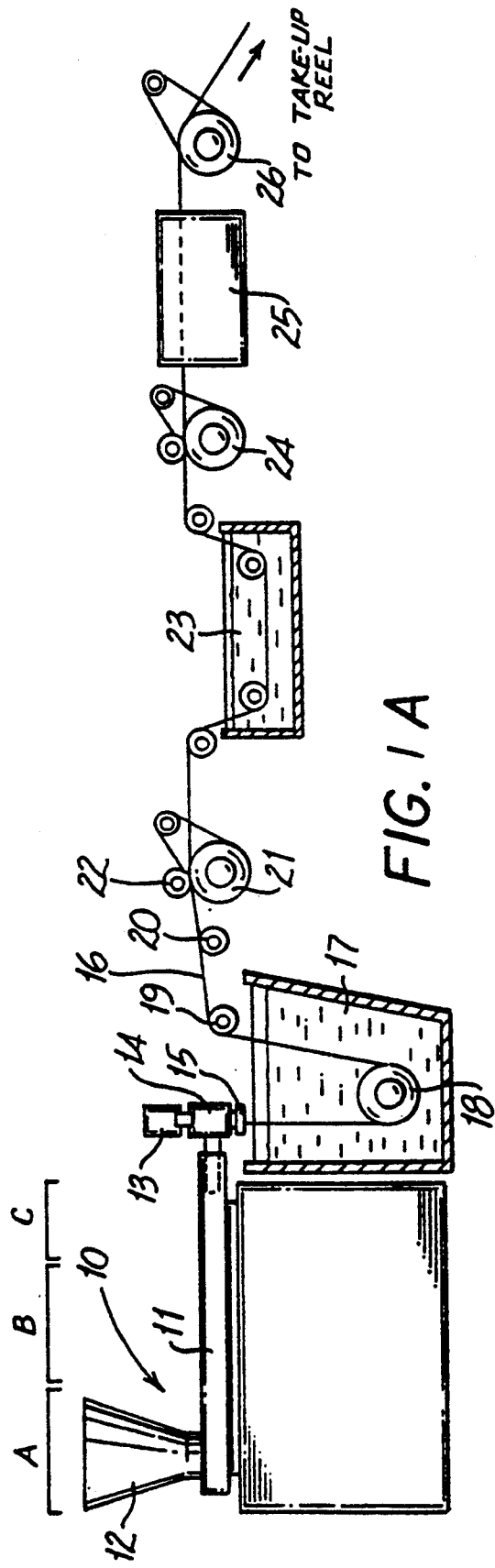
FIG. 1A is a schematic illustration of apparatus which is suitable for carrying out the polyamide monofilament suture manufacturing process of this invention; and, FIG. 1B is a modification of the apparatus of FIG. 1A which is particularly suitable for the manufacture of polyamide monofilaments of smaller size, e.g., sizes 4/0 and smaller.

FIG. 1A schematically illustrates a polyamide monofilament manufacturing operation in accordance with the invention which is especially suitable for producing larger size sutures, e.g., those of sizes 3/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polyamide resin are introduced to the extruder through hopper 12. Any of the polyamides which are useful for the formation of fibers can be used herein. Representative of such polyamides are polycaprolactam (nylon 6) and polyhexamethylene adipamide (nylon 6,6).

Motor-driven metering pump 13 delivers extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 and preferably from about 1 to about 20 cm. If desired, a chimney (not shown), or shield, can be provided to reduce the length of air gap, e.g., to from 1 to 10 cm, thereby isolating monofilament 16 from contact by air currents which might otherwise affect the cooling of the monofilament in some unpredictable manner. In general, barrel zone A of the extruder can be maintained at a temperature of from about 215° to 225° C., zone B at from about 220° to 230° C. and zone C at from about 220° to about 235° C. Additional temperature parameters include: metering pump block 13 at from about 220° to about 235° C., spin pack 14 at from about 215° to about 235° C., spinneret 15 at from about 215° to about 235° C. and quench bath at from about 35° to about 45° C.

Entering quench bath 17, monofilament 16 is passed by driven roller 18 over rollers 19 and 20 and thereafter is wrapped around a first godet 21 provided with nip roll 22 to prevent slippage which might otherwise result from the subsequent stretching operation. Monofilament 16 passing from godet 21 is stretched, e.g., with stretch ratios on the order of from about 3:1 to about 5:1 and preferably from about 3.5:1 to about 4.5:1, to effect its orientation and thereby increase its tensile strength. In the stretching operation shown in FIG. 1A, generally suitable for larger size sutures, e.g., sizes 2/0 to 3/0, monofilament 16 is drawn through hot water draw bath 23 by means of second godet 24 which rotates at a higher speed than first godet 21 to provide the desired stretch ratio. The temperature of hot water draw bath 23 is advantageously from about 60° to about 98° C. and preferably is from about 80° to about 95° C.

Figure 1B:
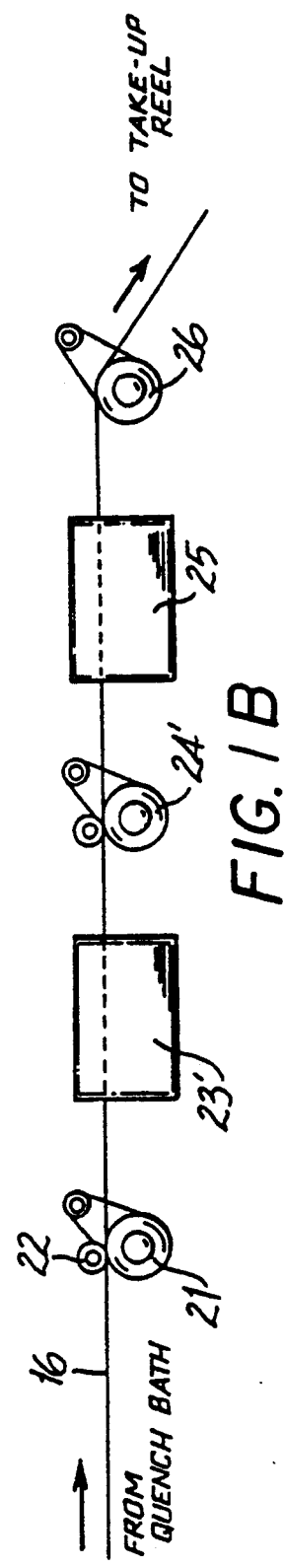

In the alternative stretching operation shown in FIG. 1B, generally preferred for smaller sutures sizes, e.g., sizes 4/0 to 8/0, monofilament 16 is drawn by second godet 24' through hot air oven chamber 23' at a temperature of from about 100° to about 185° C. and preferably from about 150° to about 170° C. to provide the desired amount of stretch. Following the stretching operation shown in FIG. 1A or 1B, monofilament 16 is subjected to an on-line annealing (relaxation) operation as a result of which the monofilament shrinks. In the processes of FIGS. 1A and 1B, annealing (relaxation) is accomplished by driving monofilament 16 by third godet 26 through second hot air oven chamber 25 at a temperature of from about 120° to about 180° C. and preferably from about 140° to about 160° C. At these temperatures, monofilament 16 will generally recover to within about 85 to about 97 percent, and preferably to within about 95 percent, of its pre-annealed length to provide the finished suture. The third godet relates at a slower speed than the second godet thus relieving tension on the filament.

If desired, the suture can be dyed in a known or conventional manner, e.g., with logwood extract and thereafter packaged and sterilized. If transportation in bulk is required after dyeing, it is preferable to collect the dyed monofilaments in skeins, not on spools, as the latter can cause damage to the suture (flattening).

The following examples are illustrative of the polyamide monofilament suture of this invention and the process for its manufacture.

EXAMPLES 1-10

Table I below sets forth typical conditions for extruding, stretching and annealing various sizes of polyamide monofilament suture in accordance with this invention. In descending order, the size of the sutures ranged from 2 to 8/0. In general, useful polyamides will possess a number average molecular weight of at least about 15,000 and a melt flow index in g/10 min of from about 3 to about 8 and preferably from about 4 to about 6. All of the sutures were fabricated from Capron 8207F (Allied Signal Corp.), a polycaprolactam having a relative viscosity of 73.9 and a moisture content of 0.062 weight percent as indicated by the manufacturer.

TABLE I

| CONDITIONS OF MANUFACTURING VARIOUS SIZES OF POLYAMIDE MONOFILAMENT SUTURE | | | | | | | | | | |
|---|---|---|---|---|---|---|---|---|---|---|
| | Example | | | | | | | | | |
| | 1 | 2 | 3 | 4 | 5 | 6 | 7 | 8 | 9 | 10 |
| | Suture Size | | | | | | | | | |
| Process Conditions | 2 | 1 | 0 | 2/0 | 3/0 | 4/0 | 5/0 | 6/0 | 7/0 | 8/0 |
| Extrusion Operation | | | | | | | | | | |
| extruder screw, rpm | 35.4 | 35.9 | 31.9 | 30.3 | 22.0 | 15.5 | 13.0 | 15.0 | 19.9 | 5.0 |
| pump rpm | 20.6 | 10.2 | 16.9 | 15.5 | 7.65 | 27.0 | 14.1 | 6.7 | 2.58 | 9.0 |
| driven roller, rpm | 6 | 7 | 8 | 10 | 10 | 11 | 11 | 12 | 6 | 14 |
| barrel temp., °C., zone A | 220 | 220 | 220 | 220 | 220 | 210 | 210 | 220 | 220 | 220 |
| barrel temp., °C., zone B | 230 | 230 | 230 | 230 | 225 | 220 | 225 | 230 | 225 | 225 |
| barrel temp., °C., zone C | 230 | 230 | 230 | 230 | 230 | 220 | 225 | 230 | 230 | 230 |
| clamp temp., °C. | 225 | 225 | 225 | 230 | 225 | 220 | 225 | 225 | 225 | 230 |
| adapter temp., °C. | 225 | 225 | 225 | 230 | 225 | 220 | 225 | 225 | 225 | 230 |
| filtration, microns | 12 | 12 | 12 | 12 | 12 | 12 | 12 | 12 | 12 | 12 |
| pump temp., °C. | 225 | 225 | 225 | 232 | 225 | 220 | 225 | 225 | 225 | 230 |
| block temp., °C. | 225 | 225 | 225 | 230 | 225 | 220 | 225 | 225 | 225 | 230 |
| spinneret temp., °C. | 230 | 220 | 225 | 230 | 230 | 225 | 225 | 220 | 225 | 225 |
| barrel melt temp., °C. | 235 | 239 | 232 | 230 | 234 | 220 | 228 | 232 | 226 | 225 |
| pump melt temp., °C. | 230 | 231 | 229 | 229 | 230 | 220 | 228 | 225 | 226 | 231 |
| spinneret melt temp., °C. | 217 | 219 | 228 | 230 | 227 | 231 | 229 | 229 | 227 | 239 |
| barrel pressure, psi | 2300 | 2687 | 2535 | 2560 | 2650 | 2590 | 2275 | 1423 | 1478 | 1000 |
| pump pressure, psi | 2540 | 2885 | 2772 | 2780 | 2890 | 2860 | 2570 | 1761 | 1776 | 970 |
| spinneret pressure, psi | 1200 | 951 | 2345 | 2050 | 2730 | 1952 | 1950 | 2000 | 2490 | 2206 |
| pump size, cc per revolution | 1.168 | 1.168 | 1.166 | 1.7 | 1.168 | .297 | .297 | .297 | .16 | .16 |
| diameter of spinneret orifices, mm | 2.0 | 2.0 | 1.25 | 1.25 | 1.25 | 0.75 | 0.75 | 0.5 | 0.304 | 0.304 |
| no. of spinneret orifices | 2 | 4 | 4 | 4 | 4 | 4 | 4 | 4 | 4 | 4 |
| lb/hr output | — | — | — | — | — | — | — | — | — | — |
| air gap, cm | 2 | 2 | 2 | 2 | 2 | 2 | 2 | 2 | 2 | .5 |
| quench bath temp., ° | 45 | 45 | 45 | 45 | 45 | 35 | 35 | 35 | 35 | 35 |

TABLE I-continued

CONDITIONS OF MANUFACTURING VARIOUS SIZES OF POLYAMIDE MONOFILAMENT SUTURE

| | Example | | | | | | | | | |
|---|---|---|---|---|---|---|---|---|---|---|
| | 1 | 2 | 3 | 4 | 5 | 6 | 7 | 8 | 9 | 10 |
| | Suture Size | | | | | | | | | |
| Process Conditions | 2 | 1 | 0 | 2/0 | 3/0 | 4/0 | 5/0 | 6/0 | 7/0 | 8/0 |
| depth of driven roller | 31 | 25 | 25 | 25 | 25 | 25 | 25 | 25 | 25 | 34 |
| Stretching (Orienting) Operation | | | | | | | | | | |
| draw bath temp., °C. | 83 | 80 | 85 | 80 | 80 | — | — | — | — | — |
| first oven chamber temp., °C. | — | — | — | — | — | 150 | 150 | 150 | 150 | 170 |
| first godet, mpm | 12.5 | 8.8 | 11.3 | 16.1 | 17.6 | 17.6 | 17.6 | 17.6 | 11.4 | 20 |
| second godet, mpm | 50 | 34.8 | 45.1 | 63.0 | 70.1 | 70.1 | 70.1 | 69.8 | 46.4 | 70.4 |
| draw ratio | 4.0 | 4.1 | 4.0 | 4.0 | 4.0 | 4.0 | 4.0 | 4.1 | 4.1 | 3.5 |
| Annealing (Relaxation) Operation | | | | | | | | | | |
| second oven chamber temp., °C. | 160 | 160 | 170 | 170 | 150 | 140 | 140 | 140 | 140 | 140 |
| third godet, mpm | 47.4 | 33.3 | 42.0 | 60.0 | 66.4 | 66.0 | 66.6 | 66.0 | 66.7 | 67.4 |

The physical properties of polyamide monofilament sutures produced in accordance with the conditions of Table I were measured at 73° F. and 50 relative humidity. Measurements of percent elongation, tensile strength and energy were carried out employing an Instron Corporation (Canton, Mass.) Tensile Tester, model no. 4301, equipped with yarn grips and operated with a gauge length of 127 mm and a crosshead speed of 127 mm/min.

The physical properties of the sutures and the procedures employed for their measurement are set forth in Table II as follows:

TABLE II

PROCEDURES FOR MEASURING PHYSICAL PROPERTIES OF POLYAMIDE MONOFILAMENT SUTURES

| Physical Property | Test Procedure |
|---|---|
| knot pull, tensile strength, kg | U.S.P. XXI, tensile strength, sutures (881) |
| straight pull, kg | ASTM D-2256, Instron Corporation |
| elongation at break, % | ASTM D-2256 |
| tensile strength, kg/mm² | ASTM D-2256, Instron Corporation Series IX Automated Materials Testing System 1.03A |
| 0-5% and 0-10% strain energies, kg-mm | ASTM D-2256, Instron Corporation Series IX Automated Materials Testing System 1.03A |
| knot security | A 2 cm loop is tied with a surgeon's square knot (1 = 1 = 1 = 1) securing the throws at 20% of the USP XXII knot strength for 2/0 nonabsorbable sutures (n = 10 loops per group). The loop is placed next to a cloth-wrapped mandrel rotating at .5 rpm. The fixtures are secured to allow contact of the cloth material against the fourth throw or, top throw, of each knot. The cloth wrapping is moistened with 37° C. water prior to the test and is periodically remoistened during the test. Each pass of the cloth across the knot (for a total of 100 passes), the knot is inspected for top throw security. For a knot to be considered secure, the 3 mm ears must not come undone and there must be no relaxation of the knot or loss of the fourth throw. |
| melt flow | ASTM D-1238 |

Table III below sets forth the physical properties of the polyamide monofilament sutures:

TABLE III

PHYSICAL PROPERTIES OF POLYAMIDE MONOFILAMENT SUTURES

| | Example | | | | | | | | | |
|---|---|---|---|---|---|---|---|---|---|---|
| | 4 | | | | 5 | | | 6 | | 7 |
| | Suture Size | | | | | | | | | |
| | 2/0 | | | | 3/0 | | | 4/0 | | 5/0 |
| | Lot No. | | | | | | | | | |
| Physical Property | 1 | 2 | 3 | 4 | 1 | 2 | 3 | 1 | 2 | 1 | 2 |
| knot pull, kg | 2.807 | 2.932 | 3.154 | 2.683 | 1.577 | 1.724 | — | 1.117 | — | .6909 | .6978 |
| elongation at break, % | 52.6 | 53.71 | 61.37 | 63.40 | 48.07 | 56.52 | 55.62 | 58.08 | 52.90 | 39.5 | 38.2 |
| tensile strength, kg | 3.441 | 3.493 | 3.540 | 3.515 | 1.705 | 1.823 | 1.699 | 1.146 | 1.179 | .8175 | .8057 |
| 0-5% energy, kg-mm | 3.273 | 1.107 | 2.342 | 2.227 | 1.45 | 1.50 | 1.418 | .9248 | .9264 | .6195 | .5713 |
| 0-10% energy, kg-mm | 8.573 | 6.206 | 6.655 | 6.383 | 3.988 | 4.030 | 3.838 | 2.387 | 2.518 | 1.703 | 1.597 |
| energy to break, kg-mm | 147.0 | 153.7 | 173.8 | 100.1 | 64.25 | 83.40 | 76.71 | 50.93 | 49.97 | 22.65 | 21.15 |
| energy to yield, kg-mm | 1.908 | 47.5 | 95.38 | 105.80 | 8.98 | 1.468 | .8041 | .3825 | .9264 | .2082 | .3657 |

COMPARATIVE EXAMPLES 1–4

Employing the same physical testing procedures described in Table II, the physical properties of sizes 2/0, 3/0, 4/0 and 5/0 of a commercially available polyamide monofilament suture (Ethicon Inc., Somerville, N.J.) were measured. The test results are set forth in Table IV as follows:

TABLE IV

PHYSICAL PROPERTIES OF KNOWN POLYAMIDE MONOFILAMENT SUTURES

| | Comparative Example | | | | | | | | | | | |
|---|---|---|---|---|---|---|---|---|---|---|---|---|
| | 1 | | | 2 | | | 3 | | | 4 | | |
| | Suture Size | | | | | | | | | | | |
| | 2/0 | | | 3/0 | | | 4/0 | | | 5/0 | | |
| | Lot No. | | | | | | | | | | | |
| Physical Property | 1 | 2 | 3 | 1 | 2 | 3 | 1 | 2 | 3 | 1 | 2 | 3 |
| elongation at break, % | 31.99 | 31.57 | 30.47 | 25.53 | 28.77 | 21.82 | 34.32 | 28.63 | 30.50 | 28.20 | 25.99 | 24.40 |
| tensile strength, kg | 4.084 | 4.025 | 3.923 | 2.406 | 2.418 | 2.222 | 1.623 | 1.544 | 1.492 | .8655 | .9310 | .8929 |
| 0–5% energy, kg-mm | 4.797 | 4.658 | 4.687 | 3.264 | 2.225 | 3.200 | 1.042 | 1.252 | .8618 | .5175 | .5630 | .6654 |
| 0–10% energy, kg-mm | 12.87 | 12.70 | 12.84 | 9.087 | 6.413 | 8.734 | 3.150 | 3.719 | 2.703 | 1.687 | 1.902 | 2.090 |
| energy to break, kg-mm | 102.00 | 99.54 | 95.11 | 49.56 | 48.71 | 36.52 | 37.78 | 29.12 | 28.24 | 15.14 | 15.04 | 13.46 |
| energy to yield, kg-mm | 80.20 | 65.54 | 57.64 | 33.95 | 13.51 | 35.29 | 6.599 | 7.079 | .4647 | 2.043 | .2788 | .1903 |

Comparing these data with the data for the equivalently sized sutures of this invention (i.e., the sutures of Examples 4–7 set forth in Table III), it is clearly evident that the latter possess significantly reduced energies compared with those of Comparative Examples 1–4. Collectively referring to the sutures of Table IV as a "standard polyamide monofilament suture", the suture of this invention will exhibit significantly reduced energy, e.g., an average of at least about 10% and preferably at least about 30% reduced 0–5% energy and/or 0–10% energy for an equivalent size of standard polyamide monofilament suture.

COMPARATIVE EXAMPLE 5

This example compares the knot security of a size 3/0 commercially available polyamide monofilament suture (Ethicon Inc., Somerville, N.J.) with that of the equivalent size of suture herein (Example 5) employing the procedure described in Table II. The results of the knot security comparison are set forth in Table V below:

TABLE V

KNOT SECURITY CHARACTERISTICS OF POLYAMIDE MONOFILAMENT SUTURES

| | Suture Size | Knot Security |
|---|---|---|
| Comparative Example 5 | 0 | 2/10 |
| Example 5 | 0 | 0/10 |

As these data show, while none of the knots (out of a total of 10 knots tested to 100 cycles) failed in the case of the suture of this invention (Example 5), 2 out of 10 of the knots formed with the suture of Comparison Example 5 ("standard polyamide monofilament suture") failed after approximately 10 cycles.

What is claimed is:

1. A process for manufacturing a polyamide monofilament suture exhibiting reduced energy and/or increased knot security which comprises the operations of extruding a polyamide resin at an extrusion temperature of from about 215° to about 275° C. to provide a monofilament, stretching the solidified monofilament at a temperature of from about 40° to about 98° C. in liquid medium or at from about 50° to about 185° C. in gaseous medium at a stretch ratio of from about 3:1 to about 5:1 to provide a stretched monofilament and annealing the stretched monofilament at a temperature of from about 100° to about 180° C. to provide the finished suture, the annealing resulting in shrinkage of the stretched monofilament for a recovery to within about 80 to about 97 percent of the length of the monofilament prior to annealing, the finished suture exhibiting reduced energy and/or increased knot security compared with the energy and/or knot strength of a suture of equivalent size obtained by a process which omits or deviates significantly from one or more of the foregoing operations.

2. The process of claim 1 wherein extruding is carried out at from about 220° to about 250° C., stretching is carried out at from about 60° to about 98° C. in liquid medium or at from about 100° to about 170° C. in gaseous medium at a stretch ratio of from about 3.5:1 to about 4.5:1 and annealing is carried out at from about 120° to about 180° C. with recovery to within about 85 to about 95 percent.

3. The process of claim 1 wherein the polyamide possesses a number average molecular weight of at least about 15,000 and a melt flow index in g/10 min of from about 3 to about 8.

4. The process of claim 1 wherein the polyamide possesses a melt flow index in g/10 min of from about 4 to about 6.

5. The process of claim 1 wherein the polyamide is a polycaprolactam or a polyhexamethylene adipamide.

6. The process of claim 1 wherein the polyamide is a polycaprolactam or a polyhexamethylene adipamide possessing a number average molecular weight of at least about 15,000 and a melt flow index in g/10 min of from about 3 to about 8.

7. The process of claim 1 wherein the polyamide is a polycaprolactam or polyhexamethylene adipamide possessing a melt flow index in g/10 min of from about 4 to about 6.

8. The process of claim 1 wherein for suture sizes of 3/0 and larger, the stretching operation is accomplished by passing the solidified monofilament through water at a temperature of from about 60° to about 98° C.

9. The process of claim 1 wherein for suture sizes of 3/0 and larger, the stretching operation is accomplished by passing the solidified monofilament through water at a temperature of from about 80° to about 95° C.

10. The process of claim 1 wherein for suture sizes of 4/0 and smaller, the stretching operation is accomplished by passing the solidified monofilament through air at a temperature of from about 100° to about 185° C.

11. The process of claim 1 wherein for suture sizes of 4/0 and smaller, the stretching operation is accomplished by passing the solidified monofilament through air at a temperature of from about 150° to about 170° C.

12. The process of claim 1 wherein the annealing operation is carried out at a temperature of from about 140° to about 180° C., the annealing resulting in shrinkage of the stretched monofilament for a recovery to within about 85 to about 97 percent of the length of the monofilament prior to annealing.

13. The process of claim 1 wherein the annealing operation is carried out at a temperature of from about 140° to about 170° C., the annealing resulting in shrinkage of the stretched monofilament for a recovery to within about 93 to about 100 percent of the length of the monofilament prior to annealing.

14. The process of claim 1 wherein the polyamide is a polycaprolactam or a polyhexamethylene adipamide, the extruding operation is carried out at a temperature of from about 215° to about 275° C., the stretching operation is carried out at a temperature of from about 60° to about 98° C. in water or at from about 100° to about 185° C. in air and a stretch ratio of from about 3.5:1 to about 5:1 and the annealing operation is carried out at a temperature of from about 120° to about 180° C. to provide a recovery to within about 85 to about 97 percent of the length of the monofilament prior to annealing.

15. The process of claim 1 wherein the polyamide is a polycaprolactam or a polyhexamethylene adipamide, the extruding operation is carried out at a temperature of from about 220° to about 250° C., the stretching operation is carried out at a temperature of from about 80° to about 95° in water or from about 150° to about 170° C. in air and a stretch ratio of from about 3.5:1 to about 4.5:1 and the annealing operation is carried out at a temperature of from about 140° to about 170° C. to provide a recovery to within about 93 to about 95 percent of the length of the monofilament prior to annealing.

* * * * *